(12) United States Patent
Perot et al.

(10) Patent No.: US 6,398,554 B1
(45) Date of Patent: Jun. 4, 2002

(54) PROCESS FOR PRODUCING A DENTAL PROSTHESIS

(75) Inventors: Jean-Marc Perot, Vienne; Michel Divet; Guy Rolet, both of Lyons, all of (FR)

(73) Assignee: Dentalmatic Technologies Inc., Montreal (CA)

( * ) Notice: Subject to any disclaimer, the term of this patent is extended or adjusted under 35 U.S.C. 154(b) by 0 days.

(21) Appl. No.: 09/331,288

(22) PCT Filed: Dec. 20, 1996

(86) PCT No.: PCT/FR98/02055
§ 371 (c)(1),
(2), (4) Date: Jan. 27, 2000

(87) PCT Pub. No.: WO98/27890
PCT Pub. Date: Jul. 2, 1998

(Under 37 CFR 1.47)

(51) Int. Cl.$^7$ .............................. A61C 5/10; A61C 5/08
(52) U.S. Cl. ....................... 433/223; 433/218
(58) Field of Search ................. 433/218, 219, 433/223

(56) References Cited

U.S. PATENT DOCUMENTS 5,314,335 A * 5/1994 Fung ............................ 433/223
5,378,154 A * 1/1995 Van Der Zel ............... 433/223
5,382,164 A * 1/1995 Stern ........................... 433/223

FOREIGN PATENT DOCUMENTS

| EP | 0311214 A1 | * | 4/1989 |
| EP | 0580565 A2 | * | 1/1994 |
| EP | 0643948 A1 | * | 3/1995 |
| FR | 2536654 A1 | * | 6/1984 |
| WO | WO-96/10371 A1 | * | 4/1996 |

* cited by examiner

Primary Examiner—John J. Wilson
(74) Attorney, Agent, or Firm—Oliff & Berridge, PLC

(57) ABSTRACT

A method for producing a dental prosthesis includes computer modeling of a three-dimensional prosthetic cap based on an human implantation zone. The method first includes casting an impression of the implantation zone of the human body. Then, on the basis of the moulded impression, a digital three-dimensional representation ($R_1$) of the implantation zone is made by sensing the implantation zone with a sensor. From this, a digital representation ($R_{1c}$) of the internal surface of the prosthesis is defined on the basis of the digital three-dimensional representation ($R_1$) of the implantation zone. A digital three-dimensional representation ($R_2$) of the external surface of the prosthesis is then defined on the basis of the surrounding parameters of the prosthesis and the digital three-dimensional representation ($R_{1c}$). Then, a digital three-dimensional representation ($R_3$) of the external surface of the cap is defined on the basis of the external ($R_2$) and internal ($R_{1c}$) surfaces of the prosthesis, taking into account the criteria of the mechanical and aesthetic characteristics which the cap must have. Based on this three-dimensional model, an actual prosthetic cap can be produced if the cap meets certain requirements.

8 Claims, 2 Drawing Sheets

PROCESS FOR PRODUCING A DENTAL PROSTHESIS

The present invention relates to the field of dentistry, and more particularly concerns prostheses of the fixed or connected type, such as bridges, crownwork, false stumps, implants or removal/nonremovable dentures.

For economic reasons, it has most often been proposed to produce dental prostheses from a precious, semiprecious or nonprecious metal alloy, such as from nickel-chromium alloy or cobalt-based alloy.

For obvious aesthetic reasons, the design of such a prosthesis, which was purely of metallic nature, has developed to involve the manufacture of a cap which is still of metallic structure but is covered by a ceramic crown. The cap has a profile tailored to the implantation zone of the human body. The profile of the cap is produced on the basis of an impression of the implantation zone.

It is clear that there are a number of drawbacks with the manufacture of such prostheses, in particular because of the extent of work inside the mouth, significant production delays, high labour cost, misunderstandings between the dentist and the technician and a need for a plurality of operations in the mouth, which are time-consuming and uncomfortable for the patient.

In order to overcome the drawbacks mentioned above, solutions have been envisaged in the prior art with the aim of automating the manufacture of such prostheses.

Document EP-A-643 948 relates to a process for producing a dental prosthesis comprising a cap and a crown. The cap comprises an internal surface which is duplicate of the shape of the stump to be fitted out, and an external surface which is a mathematical enlargement of the surface of the stump.

The document FR-A-2 536 654 has thus described a process for producing a dental prosthesis consisting, in a first stage, in recording the shape of the implantation zone using an impression, microsensor or optical impression then, in a second stage, in automatically machining the prosthetic article while taking into account the recorded data and information provided by processing software. According to a first alternative embodiment, it is proposed to machine, on the one hand, the internal face of the cap to the shape of the implantation zone and the external face of the crown as a function of the envelope and the bite. The cap and the crown are selected from a supply of crowns and caps which are paired so that the external face of the cap has the same profile as the internal face of the crown.

This document describes, in particular, a second alternative embodiment which consists, on the basis of a recording of the shapes taken in the mouth, in machining the internal and external faces of the metal cap in a metal block, in taking a new recording of the external face of the metal crownwork, in machining the internal face of the crown as a function of this and from a ceramic block, then, as a function of the envelope and the bite, in machining the external face of it before assembling the metal cap with the ceramic crown.

Although such a document describes a process for automatic production of a dental prosthesis, it is apparent that there are drawbacks with the practical implementation of such a process. It should firstly be pointed out that, according to its first alternative embodiment, such a process requires the provision of a supply of crowns and caps to be paired, the number of which may be relatively high in order to try to cover all the prostheses configurations to be produced. However, it proves impossible in practice to provide a supply of prostheses matching all the morphologies of implantation zones. Furthermore, the second alternative embodiment requires the use of a plurality of manufacturing operations.

More fundamentally, it should be pointed out that the metal cap is generally produced homothetically with the implantation zone, whereas the crown has an external surface matched to the envelope of the buccal environment. The Applicant Company has pointed out that such an approach led in certain cases to the production of crowns having localized zones of reduced strength, the presence of which unequivocally affects the reliability of the prostheses produced in this way. In addition, this technique sometimes leads to obtaining unaesthetic prostheses, because of the fact that it is impossible, at least locally, to produce the crown in ceramic. There is therefore an apparent need to provide a manufacturing method designed, on the one hand, to take into account the clinical situation of the tooth to be fitted out and, on the other hand, to comply with the rules of aesthetics and the criteria of mechanical durability which ceramic crowns need to satisfy in order to provide long-term reliability.

The object of the invention is therefore to provide a process for producing a dental prosthesis, designed to make it possible to define the profile of the cap and of a crown while respectively taking account of the implantation zone and the environment of the prosthesis, while guaranteeing optimization of the profile of the cap in order to guarantee compliance with the criteria of mechanical durability and aesthetics of the crown.

To achieve this object, the process according to the invention is designed to allow the production of a dental prosthesis having at least, on the one hand, a prosthetic cap intended to be fitted on an implantation zone of the human body and, on the other hand, a prosthetic crown supported by the cap.

According to the invention, the process comprising:

defining a three-dimensional representation of the internal surface of the prosthesis, corresponding to the internal surface of the cap defined on the basis of the digitized three-dimensional representation of the implantation zone, while taking account of the rules connected with the insertion and sealing of a prosthesis, defining a digitized three-dimensional representation of the external surface of the prosthesis, on the basis of the environmental parameters of the prosthesis while taking account of the constraints resulting from the internal surface of the prosthesis, consisting of the internal surface of the cap and of the digitized three-dimensional representation of the internal surface of the prosthesis, and in defining a digitized three-dimensional representation of the external surface of the cap, on the basis of the external surface of the prosthesis, while taking account of the internal surface of the prosthesis, the criteria pertaining to mechanical durability in particular thickness, and aesthetic criteria.

The process according to the invention therefore has the advantage of making it possible to define a cap while taking into account the anatomical profile of the implantation zone, the external surface of the crown and production criteria for the crown, with a view to obtaining a prosthesis which is reliable in the long term. The subject of the invention also has the advantage of making it possible to determine, without requiring the manufacture of a prosthesis and on the basis of clinical information, whether it is possible to produce the cap and the crown under acceptable conditions of reliability and aesthetics. Such a process thus provides the possibility of choosing and adapting the profile of the cap as a function of the production conditions for the crown.

Various other characteristics will emerge from the description given below with reference to the appended drawings which, by way of non-limiting examples, show embodiments and implementations of the subject of the invention:

Figure 1:
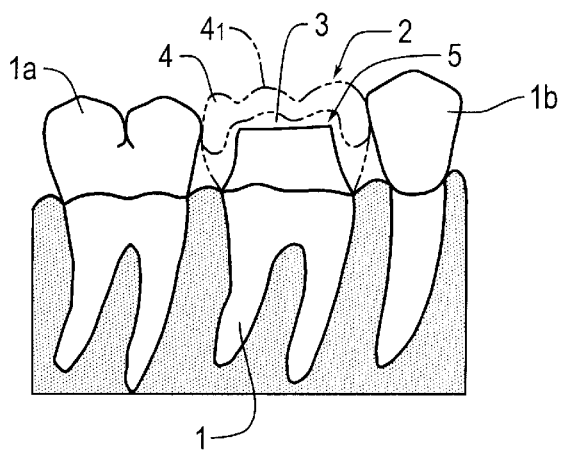
FIG. 1 is a schematic view illustrating the way in which a prosthesis is put on a tooth to be fitted out.

FIG. 1 shows an example of a tooth 1 to be fitted out using a prosthesis 2 according to the invention, having a prosthetic fitting cap 3 on which a prosthetic crown 4 is mounted.

In order to make a dental prosthesis of the type in FIG. 1, the tooth 1 to be fitted out is prepared in the conventional way. In the example illustrated, the tooth 1 to be fitted out has an implantation zone 5 for the prosthesis 2 which, in the example illustrated, consists of a stump. It is of course clear that the part of the human body used as an implantation zone 5 may have a different form, such as in particular a cavity, or no stump (bridgework).

Figure 2:
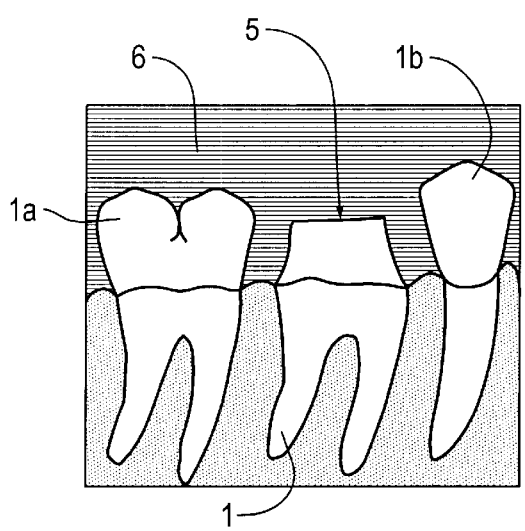
FIGS. 2 to 4 are schematic views which each show one characteristic step of the process according to the invention.

As more precisely shown in FIG. 2, the process according to the invention consists in producing an impression of at least the implantation zone 5 using a moulding 6. The mould 6 is produced in any of the ways known to the person skilled in the art, with a view to obtaining at least one profile representative of the implantation zone 5, namely the stump in the example illustrated. Besides knowing the clinical situation specifically connected with the implantation zone, provision may also be made to gather all the clinical information relating to the production of the prosthesis, such as that relating, for example, to the position of the adjacent teeth $1a$, $1b$ and/or the antagonistic teeth in a static and/or dynamic occlusion position. This step of the process therefore aims to gather, using one or more moulding operations and possible clinical and/or morphological measurements (mandibular kinematics, line of the smile, etc.), the information relating to the implantation and integration of the prosthesis inside the patient's mouth.

Figure 3:
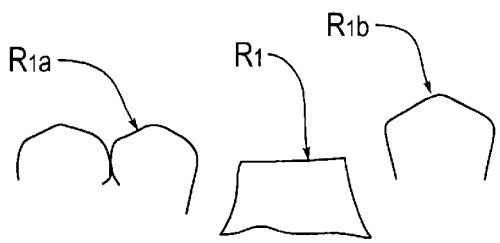

On the basis of the moulded impression 6, the process according to the invention proposes establishing a digitized three-dimensional representation $R_1$ of at least the implantation zone 5. The digitized representation $R_1$ of the implantation zone, which is illustrated in FIG. 3, is obtained using a sensor, preferably of optical nature, making it possible to take measurements of the moulded impression 6 with a view to obtaining the three-dimensional definition of the implantation zone 5. It should be noted that the measurements may be taken directly from the negative impression produced by the mould 6 with a profile complementary to that of the stump, or from a positive mould which reproduces the stump and is obtained from the negative mould 6. The sensor used transmits the measurements, after conversion, to a computer which stores the digital three-dimensional data characterizing the implantation zone 5. The computer, which is equipped with a screen, is designed to display a three-dimensional representation $R_1$ of the implantation zone 5. In the case when clinical information about the environment of the implantation zone 5 is gathered, it is proposed to provide a digitized representation of this, such as for example $R_{1a}$, $R_{1b}$ for the adjacent and/or antagonistic teeth.

The process according to the invention then consists in defining a digitized three-dimensional representation $R_{1c}$ of the internal surface of the prosthesis, defined on the basis of the digitized representation $R_1$ of the implantation zone, while taking account of the rules connected with the insertion and sealing of a prosthesis. Provision may thus be made, in particular, to leave a space remaining between the digitized representation $R_1$ of the implantation zone and the digitized representation $R_{1c}$ of the internal surface of the prosthesis, in order to put the sealing cement in place.

Figure 4:
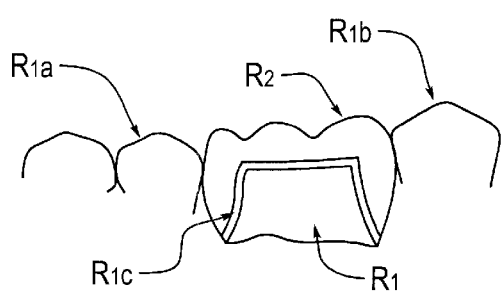
Figure 5:
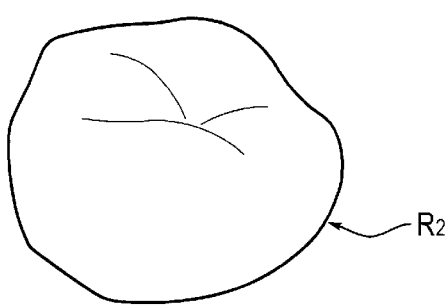
FIG. 5 is a perspective view showing the process step carried out in FIG. 4.

The process according to the invention then consists in defining a digitized three-dimensional representation $R_2$ of the external surface of the prosthesis, on the basis of the environmental parameters of the prosthesis and of the digitized three-dimensional representation $R_{1c}$ of the internal surface of the prosthesis. As can be seen more precisely from FIGS. 4 and 5, the digitized representation $R_2$ makes it possible to display the external surface of the prosthesis in relation to the digitized representation $R_1$ of the implantation zone 5, and possibly representations of the adjacent and/or antagonistic teeth such as, for example, $R_{1a}$, $R_{1b}$. The external surface of the prosthesis is therefore determined by starting with the possible measurements taken from the moulded impression and a statistically representative or acceptable morphology of the prosthesis to be produced to which deformation laws based on clinical criteria accepted by the person skilled in the art are applied. For example, provision may be made to use the criteria as defined in dental anatomy courses. It should be noted that the volume contained between the surface $R_{1c}$ and the surface $R_2$ is representative of the total volume of the prosthesis.

Figure 6:
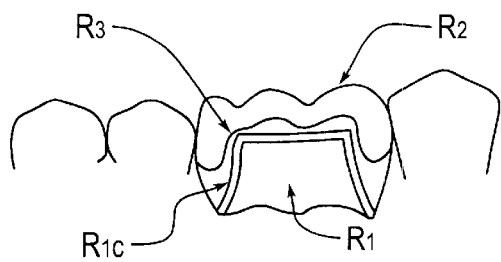
FIGS. 6 and 7 are sectional and perspective views illustrating another step of the process according to the invention.
Figure 7:
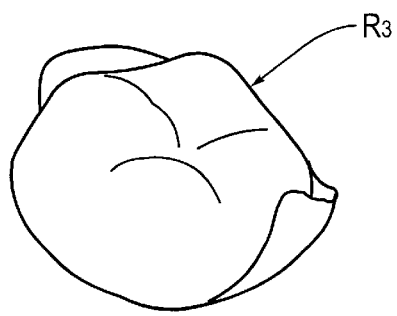
Figure 8:
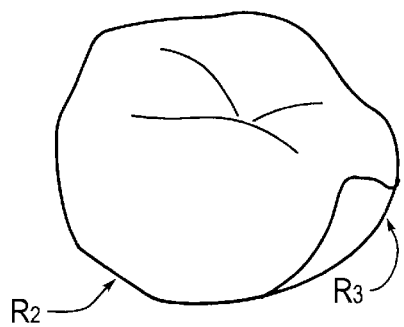
FIG. 8 is a perspective view showing an illustrative embodiment of a representation of a prosthesis to be produced.

The subject of the invention then consists in determining a digitized three-dimensional representation $R_3$ of the external surface of the prosthetic cap 3, on the basis of the digitized representation $R_{1c}$ of the internal surface of the prosthesis and of the representation $R_2$ of the external surface of the prosthesis. The digitized representation $R_3$ of the external surface of the cap, an example of which is illustrated by FIGS. 6 and 7, is produced while taking account of the criteria which need to be satisfied for the definition of the crown 4 which corresponds to the volume contained between the representations $R_3$ and $R_2$. For the definition of the crown, the criteria to be satisfied are, for example, the rules connected with aesthetics or with the shape and with the minimum and/or maximum thickness which the crown must have as a function of the nature of the material used. Satisfying these criteria makes it possible to avoid the presence of fragile zones, with a view to obtaining a prosthesis which is reliable in the long term. The process according to the invention also has the advantage of knowing whether, before proceeding with manufacture of the prosthesis, it is possible to produce a prosthesis which satisfies the anatomical requirements of the buccal environment and the mechanical and aesthetic constraints connected with the production of the prosthesis. Thus, as illustrated in FIG. 8, provision may be made to make a digitized representation of the prosthesis 2 on the basis of the digitized representations $R_2$, $R_3$, respectively of the external surface of the prosthesis and of the external surface of the cap.

It should of course be considered that the digitized representation $R_3$ of the external surface of the cap is provided by suitable programming means taking into account the digitized representations $R_{1c}$, $R_2$, respectively, of the internal surface of the prosthesis and of the external surface of the prosthesis and the previously stored manufacturing criteria for the crown. It should be noted that the volume contained between the surface $R_{1c}$ and the surface $R_3$ is representative of the total volume of the cap.

Figure 9:
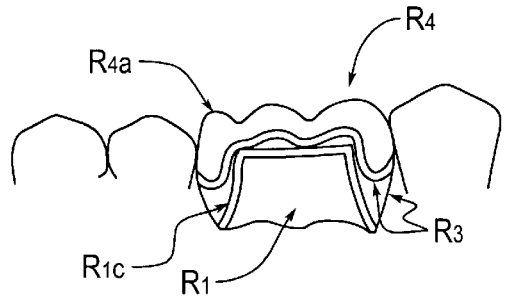
FIG. 9 is a sectional view illustrating another step of the process according to the invention.

According to another advantageous characteristic of the invention, which is illustrated in FIG. 9, the process according to the invention also consists in defining a digitized three-dimensional representation $R_{4a}$ of the internal surface of the crown, defined on the basis of the digitized representation $R_3$ of the external surface of the cap, while taking account of the rules connected with the insertion and sealing of a crown on a cap. Provision may thus be made, in particular, to leave a space between the digitized representation $R_{4a}$ of the internal surface of the crown and the digitized representation $R_3$ of the external surface of the cap in order to put the sealing cement in place.

The process according to the invention then consists in defining a digitized three-dimensional representation $R_4$ of the external surface of the crown, defined on the basis of the digitized representation $R_2$ of the external surface of the prosthesis and on the external boundary of the digitized representation $R_{4a}$ of the internal surface of the crown. It should be noted that the volume contained between the surface $R_{4a}$ and the surface $R_4$ is representative of the total volume of the crown. The digitized representations $R_{4a}$ and $R_4$ are of course obtained using suitable programming means.

Figure 11:
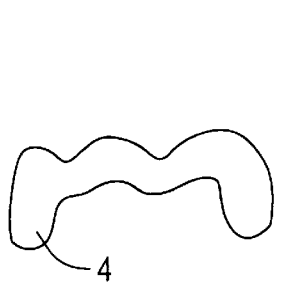
FIGS. 10 and 11 show illustrative embodiments of the elements of a prosthesis, which are obtained according to the process according to the invention.
Figure 10:
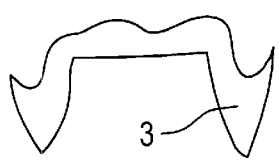

When the three-dimensional digitized representation $R_3$ of the cap 3 has been chosen, it is possible to proceed with machining a corresponding prosthetic cap 3 (FIG. 10). In this case, the cloud of points corresponding to the three-dimensional digitized representation $R_3$ of the external surface of the cap, and the cloud of points corresponding to the three-dimensional digitized representation $R_{1c}$, of the internal surface of the prosthesis are delivered to any kind of system capable of processing the digital information, such as a numerically controlled machine. It is similarly possible to proceed with machining a corresponding prosthetic crown 4 (FIG. 11). In this case, the cloud of points corresponding to the three-dimensional digitized representation $R_4$a of the internal surface of the crown and the cloud of points corresponding to the three-dimensional digitized representation $R_4$ of the external surface of the crown are delivered to some kind of system capable of processing the digital information.

Figure 12:
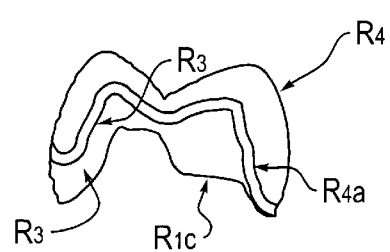
FIG. 12 is a section showing one advantage of the process according to the invention.

The definition of the cap 3, according to the process according to the invention, makes it possible to optimize its production, from both the mechanical and from the aesthetic point of view. The cap 3 can thus have an anatomical internal profile satisfying clinical information, and also an external profile satisfying the criteria, in particular, of mechanical durability and aesthetics for the production of the crown 4. In the same sense and as clearly shown by FIG. 12, such a process makes it possible to compensate automatically for the defects of an implantation zone, by making it possible to produce a digitized representation $R_3$ of the external surface of the cap which matches the morphology of the implantation zone while giving the crown 4 a constant thickness. Another advantage of the process according to the invention is that it makes it possible either to choose the machining parameters as a function of the constraints connected with the surfaces to be machined, or to adapt the profile of the surfaces to be machined as a function of the machining method.

In the example considered above, the prosthesis consists of two distinct parts, namely a cap 3 and a crown 4. It should be noted that the process according to the invention can be implemented in the case of a prosthesis which does not have two separate parts. It may thus be envisaged to determine a digitized three-dimensional representation $R_3$ of the external surface of the cap, in such a way that it is at least locally underdimensioned in relation to the external surface of the prosthesis determined by the digitized three-dimensional representation $R_2$. The prosthetic cap 3 produced on the basis of this digitized representation therefore has at least localized underdimensioning making it possible to add material on the cap. This addition of material constitutes the crown and is generally processed or machined in order to give the prosthesis its final aesthetic appearance.

In another embodiment of the invention, provision may be made to determine a digitized three-dimensional representation $R_3$ of the external surface of the cap, in such a way that it is at least locally overdimensioned in relation to the external surface of the prosthesis determined by the digitized three-dimensional representation $R_2$. The prosthetic cap 3 produced on the basis of this digitized representation has an at least localized overthickness, which is then processed by removing material to form the final prosthetic crown. In this illustrative embodiment, the prosthetic cap and the prosthetic crown form a single piece.

The two illustrative embodiments above allow aesthetic optimization of the prosthesis while providing the possibility of processing or machining the prosthetic crown which is formed by either adding or removing material. It is of course clear that material may be both added and removed simultaneously in order to produce one and the same prosthesis.

In the description above, the process according to the invention was described in relation to the manufacture of a prosthesis involving a single tooth. It should of course be understood that the process according to the invention may be implemented for a plural prosthesis. In this case, it should be noted that the various steps of the process according to the invention may be implemented in order to produce the various teeth of the plural prosthesis one after the other. Similarly, each step of the process may be applied for all the teeth in the prosthesis.

The invention is not limited to the examples which have been described and represented as various modifications may be made to them without departing from its scope.

What is claimed is:

1. A process for the production of a dental prosthesis having at least a prosthetic cap intended to be fitted on an implantation zone of the human body and a prosthetic crown supported by the cap, wherein the process comprises:

sensing the implantation zone with a sensor to obtain implantation zone measurement data used in producing a digitized three-dimensional representation ($R_1$) of the implantation zone, defining a three-dimensional representation of an internal ($R_{1c}$) surface of the prosthesis, corresponding to an internal surface of the cap on the basis of the digitized three-dimensional representation ($R_1$) of the implantation zone, while taking account of rules connected with the insertion and sealing of the prosthesis, defining a digitized three-dimensional representation ($R_2$) of an external surface of the prosthesis, on the basis of environmental parameters of the prosthesis, while taking account of the constraints from the internal surface ($R_{1c}$) of the prosthesis, consisting of the internal surface of the cap, and defining a digitized three-dimensional representation ($R_3$) of the external surface of the cap, on the basis of the external surface ($R_2$) of the prosthesis, while taking into account of the internal surface ($R_{1c}$) of the prosthesis, the criteria pertaining to mechanical durability, including thickness, and aesthetic criteria to form a three-dimensional digitized model of the prostic cap.

2. The process according to claim 1, further comprising:

defining a digitized three-dimensional representation ($R_{4a}$) of an internal surface of the crown, defined on the basis of the digitized three-dimensional representation ($R_3$) of the external surface of the cap, while taking account of the rules connected with the insertion and sealing of a crown on the cap, and defining a digitized three-dimensional representation ($R_4$) of an external surface of the crown, defined on the basis of the external surface ($R_2$) of the prosthesis, while taking account of the external boundaries of the internal surface ($R_{4a}$) of the crown.

3. The process according to claim 2, wherein the corresponding prosthetic crown is produced on the basis of the definition of the digitized three-dimensional representation ($R_{4a}$) of the internal surface of the crown and of the digitized three-dimensional representation ($R_4$) of the external surface of the crown.

4. The process according to claim 1, wherein the corresponding prosthetic cap is produced on the basis of the definition of the digitized three-dimensional representation ($R_3$) of the external surface of the cap and of the digitized three-dimensional representation ($R_{1c}$) of the internal surface of the prosthesis.

5. The process according to claim 4, further comprising:

determining the digitized three-dimensional representation ($R_3$) of the external surface of the cap, in such a way that it is at least locally under-dimensioned in relation to the external surface of the prosthesis determined by the digitized three-dimensional representation ($R_2$), and, after the production of the prosthetic cap, producing the prosthetic crown using addition of material deposited on the prosthetic cap.

6. The process according to claim 4, further comprising:

determining the digitized three-dimensional representation ($R_3$) of the external surface of the cap, in such a way that it is at least locally over-dimensioned in relation to the external surface of the prosthesis determined by the digitized three-dimensional representation ($R_2$), and, after the production of the prosthetic cap, producing the prosthetic crown using removal of material from the prosthetic cap.

7. The process according to claim 1, wherein a plural dental prosthesis having various constituent elements is produced.

8. The process according to claim 1, further comprising a step of casting an impression of the implantation zone, wherein the step of sensing senses the implantation zone from the casting.

* * * * *

UNITED STATES PATENT AND TRADEMARK OFFICE
CERTIFICATE OF CORRECTION

PATENT NO. : 6,398,554 B1
DATED : June 4, 2002
INVENTOR(S) : Jean-Marc Perot et al.

It is certified that error appears in the above-identified patent and that said Letters Patent is hereby corrected as shown below:

<u>Title page,</u>
Item [75], Inventors, change "Michel Divet; Guy Rolet, both of Lyons" to
-- Michel Divet; Guy Rolet, both of Lyon --.

Item [85], PCT No., change "PCT/FR98/02055" to -- PCT/FR96/02055 --.

Signed and Sealed this

Eighth Day of October, 2002

*Attest:*

JAMES E. ROGAN
*Attesting Officer*      *Director of the United States Patent and Trademark Office*